United States Patent [19]
Klingemann et al.

[11] Patent Number: 5,800,368
[45] Date of Patent: Sep. 1, 1998

[54] SLEEPING DEVICE FOR INFANTS HAVING TRACHEA MALACIA AND/OR GASTRO-INTESTINAL REFLUX

[76] Inventors: Michael E. Klingemann; Alisa A. Klingemann, both of 11711 Barrington Way, Austin, Tex. 78759

[21] Appl. No.: 813,413

[22] Filed: Mar. 10, 1997

[51] Int. Cl.⁶ .................. A61F 5/00; A47C 70/02
[52] U.S. Cl. .................. 602/1; 5/655; 128/875; 128/845
[58] Field of Search .................. 602/1, 5, 15; 128/845, 128/846, 870, 872, 875; 482/23, 142; 5/603, 648, 417, 420, 669, 655, 903

[56] References Cited

U.S. PATENT DOCUMENTS

| | | | |
|---|---|---|---|
| 3,729,752 | 5/1973 | Huggins | 5/655 X |
| 4,441,221 | 4/1984 | Enste et al. | 5/431 |
| 4,471,767 | 9/1984 | Guimond | 5/655 X |
| 4,566,449 | 1/1986 | Smith | 5/655 X |
| 4,667,356 | 5/1987 | Holmquist | 5/655 |
| 4,862,535 | 9/1989 | Roberts | 5/655 |
| 5,014,376 | 5/1991 | Doran et al. | 5/655 X |
| 5,029,350 | 7/1991 | Edelson | 5/420 X |
| 5,439,008 | 8/1995 | Bowman | 128/845 X |
| 5,537,702 | 7/1996 | Brown-Milants et al. | 128/878 X |
| 5,551,108 | 9/1996 | Butler, III | 5/655 |

*Primary Examiner*—Richard J. Apley
*Assistant Examiner*—Denise Pothier

[57] ABSTRACT

A sleeping device for infants having trachea malacia and/or gastro-intestinal reflux including a foam wedge having a cutout formed therein. A plastic casing is dimensioned for securement over the foam wedge. A fabric cover is dimensioned for removable coupling over the plastic casing and the foam wedge. The fabric cover includes a pad for positioning within the cutout of the foam wedge.

1 Claim, 3 Drawing Sheets

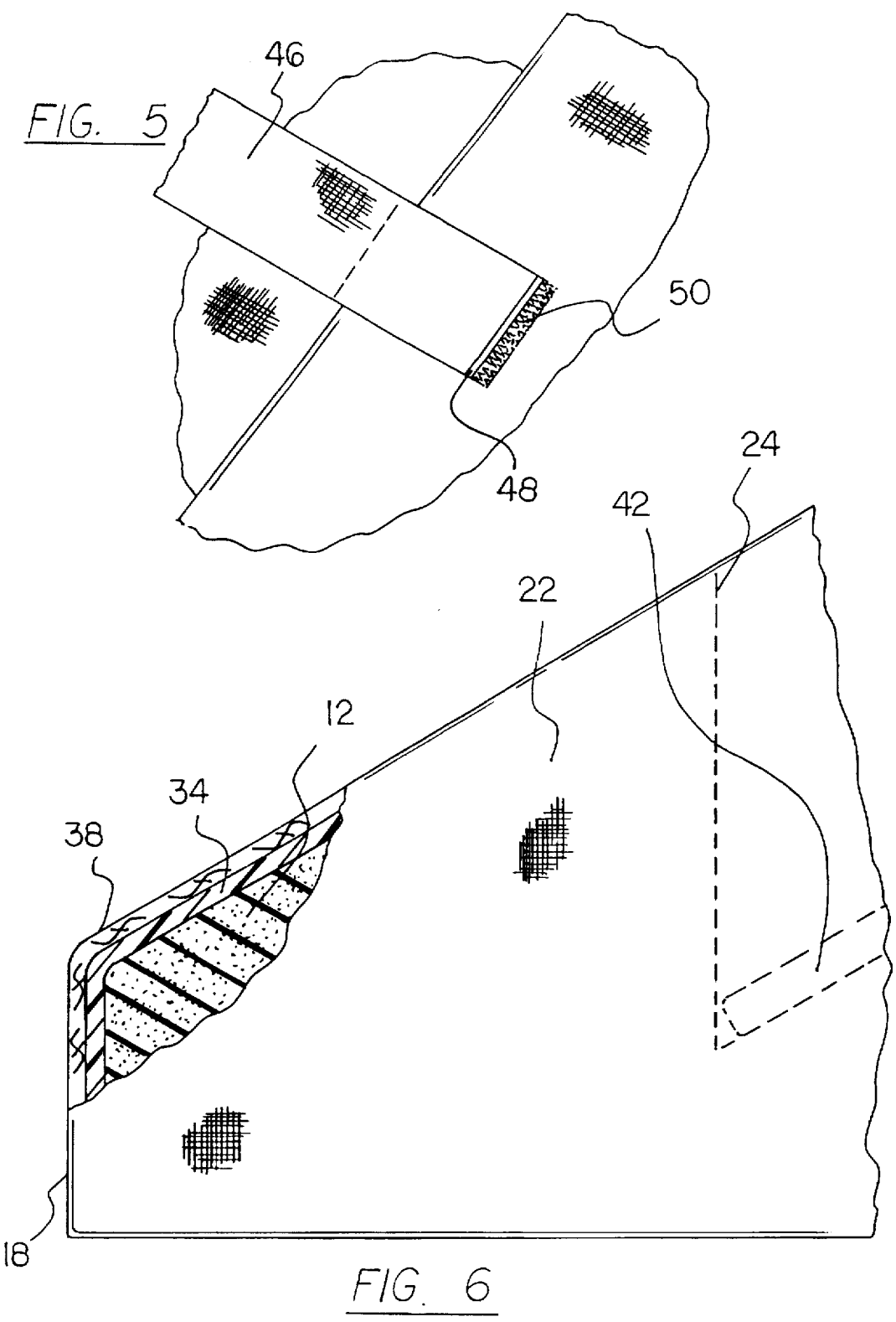

SLEEPING DEVICE FOR INFANTS HAVING TRACHEA MALACIA AND/OR GASTRO-INTESTINAL REFLUX

BACKGROUND OF THE INVENTION

1. Field of the Invention

The present invention relates to a sleeping device for infants having trachea malacia and/or gastro-intestinal reflux and more particularly pertains to allowing an infant to sleep on their side to control trachea malacia, reflux and apnea problems with a sleeping device for infants having trachea malacia and/or gastro-intestinal reflux.

2. Description of the Prior Art

The use of infant sleeping devices is known in the prior art. More specifically, infant sleeping devices heretofore devised and utilized for the purpose of preventing injuries to infants are known to consist basically of familiar, expected and obvious structural configurations, notwithstanding the myriad of designs encompassed by the crowded prior art which have been developed for the fulfillment of countless objectives and requirements.

By way of example, U.S. Pat. No. Des. 281,833 to Carney discloses the ornamental design for a baby sling and harness for infants with gastro-esophageal reflux.

U.S. Pat. No. 4,441,221 to Enste et al. discloses a child support wedge.

U.S. Pat. No. 4,667,356 to Holmquist discloses an adjustable infant bed and seat.

U.S. Pat. No. 5,029,351 to Weber discloses a baby support pillow.

U.S. Pat. No. 5,133,098 to Weber discloses an inflatable baby support pillow.

U.S. Pat. No. 4,320,543 to Dixon discloses a medical pillow.

While these devices fulfill their respective, particular objective and requirements, the aforementioned patents do not describe a sleeping device for infants having trachea malacia and/or gastro-intestinal reflux for allowing an infant to sleep on their side to control trachea malacia, reflux and apnea problems.

In this respect, the sleeping device for infants having trachea malacia and/or gastrointestinal reflux according to the present invention substantially departs from the conventional concepts and designs of the prior art, and in doing so provides an apparatus primarily developed for the purpose of allowing an infant to sleep on their side to control trachea malacia, reflux and apnea problems.

Therefore, it can be appreciated that there exists a continuing need for a new and improved sleeping device for infants having trachea malacia and/or gastrointestinal reflux which can be used for allowing an infant to sleep on their side to control trachea malacia, reflux and apnea problems. In this regard, the present invention substantially fulfills this need.

SUMMARY OF THE INVENTION

In the view of the foregoing disadvantages inherent in the known types of infant sleeping devices now present in the prior art, the present invention provides an improved sleeping device for infants having trachea malacia and/or gastro-intestinal reflux. As such, the general purpose of the present invention, which will be described subsequently in greater detail, is to provide a new and improved sleeping device for infants having trachea malacia and/or gastrointestinal reflux and method which has all the advantages of the prior art and none of the disadvantages.

To attain this, the present invention essentially comprises a foam wedge comprising an upper wall, a lower wall, a front wall, a back wall, and opposed side walls. The upper wall is angled upwardly from the front wall to the back wall at an angle of about forty-five degrees. The upper surface has a cutout formed therein. The cutout extends from a position integral with the back wall to a position inward the front wall. The cutout has an upper portion, a lower portion and an inwardly angled intermediate portion therebetween. The upper portion has a width about 1.5 times greater than a width of the lower portion. The upper portion has a length greater than a length of the lower portion. A plastic casing is dimensioned for securement over the foam wedge. A fabric cover is dimensioned for removable coupling over the plastic casing and the foam wedge. The fabric cover includes a zippered opening extending along a back and a bottom thereof to facilitate removal from the foam wedge. The fabric cover includes a pad for positioning within the cutout of the foam wedge. A strap is secured to the fabric cover at a position adjacent to where the fabric cover is over the cutout of the foam wedge. A free end of the strap has a hook and loop portion thereon. The hook and loop portion couples with a patch of hook and loop material secured on an opposing side of where the fabric cover is over the cutout of the foam wedge.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sleeping device for infants having trachea malacia and/or gastro-intestinal reflux which has all the advantages of the prior art infant sleeping devices and none of the disadvantages.

It is another object of the present invention to provide a new and improved sleeping device for infants having trachea malacia and/or gastrointestinal reflux which may be easily and efficiently manufactured and marketed.

It is a further object of the present invention to provide a new and improved sleeping device for infants having trachea malacia and/or gastro-intestinal reflux which is of durable and reliable construction.

An even further object of the present invention is to provide a new and improved sleeping device for infants having trachea malacia and/or gastro-intestinal reflux which is susceptible of a low cost of manufacture with regard to both materials and labor, and which accordingly is then susceptible of low prices of sale to the consuming public, thereby making such an sleeping device for infants having trachea malacia and/or gastro-intestinal reflux economically available to the buying public.

Even still another object of the present invention is to provide a new and improved sleeping device for infants having trachea malacia and/or gastrointestinal reflux for allowing an infant to sleep on their side to control trachea malacia, reflux and apnea problems.

Lastly, it is an object of the present invention to provide a new and improved sleeping device for infants having trachea malacia and/or gastro-intestinal reflux including a foam wedge having a cutout formed therein. A plastic casing is dimensioned for securement over the foam wedge. A fabric cover is dimensioned for removable coupling over the plastic casing and the foam wedge. The fabric cover includes a pad for positioning within the cutout of the foam wedge.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a sectional view as taken from circle 5 of FIG. 1.

FIG. 6 is a sectional view as taken from circle 6 of FIG. 4.

The same reference numerals refer to the same parts through the various Figures.

DESCRIPTION OF THE PREFERRED EMBODIMENT

Figure 1:
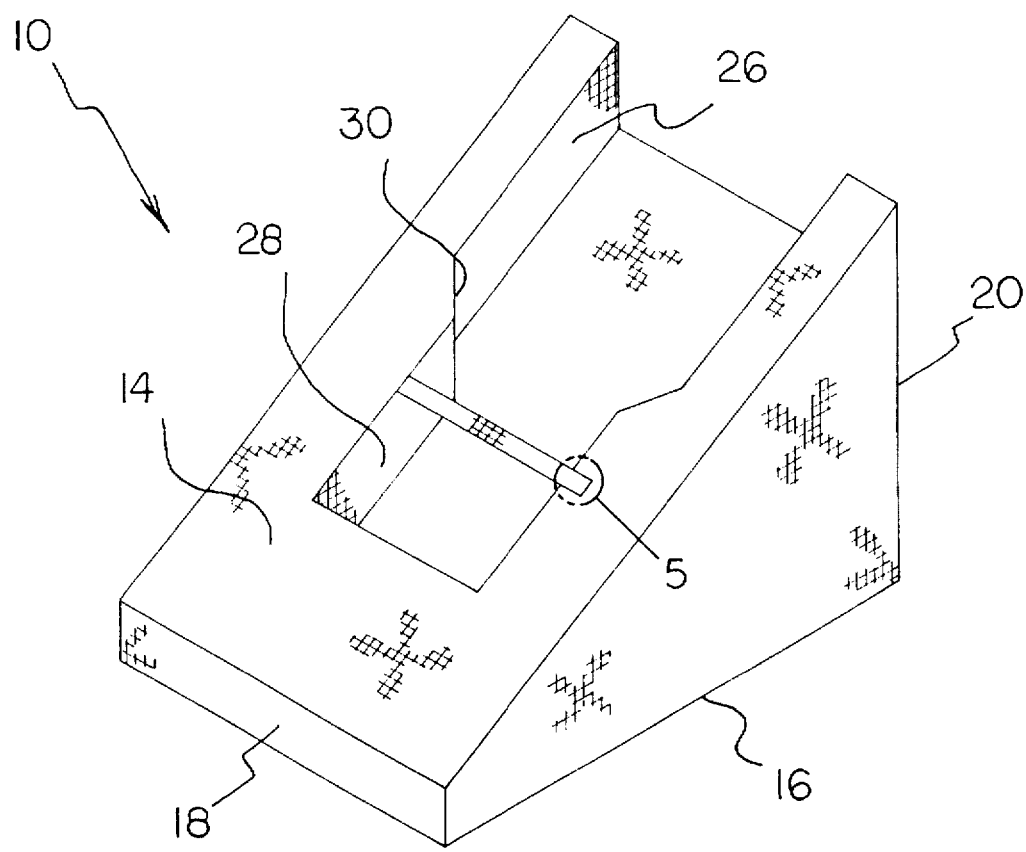
FIG. 1 is a perspective view of the preferred embodiment of the sleeping device for infants having trachea malacia and gastro-intestinal reflux constructed in accordance with the principles of the present invention.
Figure 2:
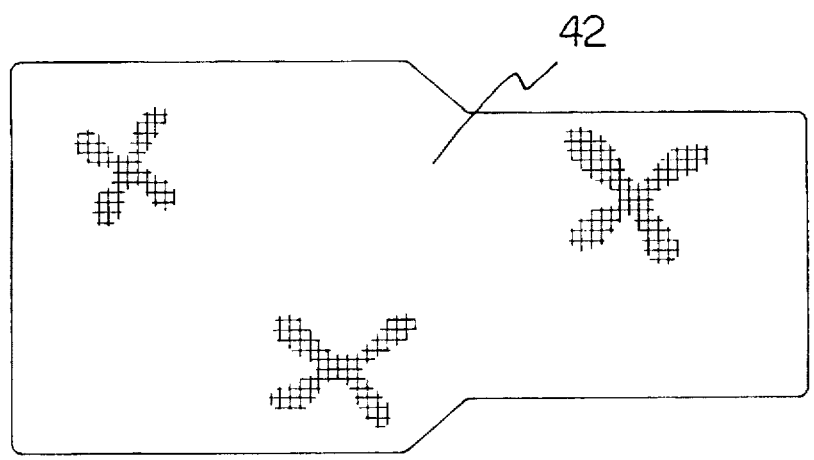
FIG. 2 is a plan view of the quilted insert of the present invention.
Figure 3:
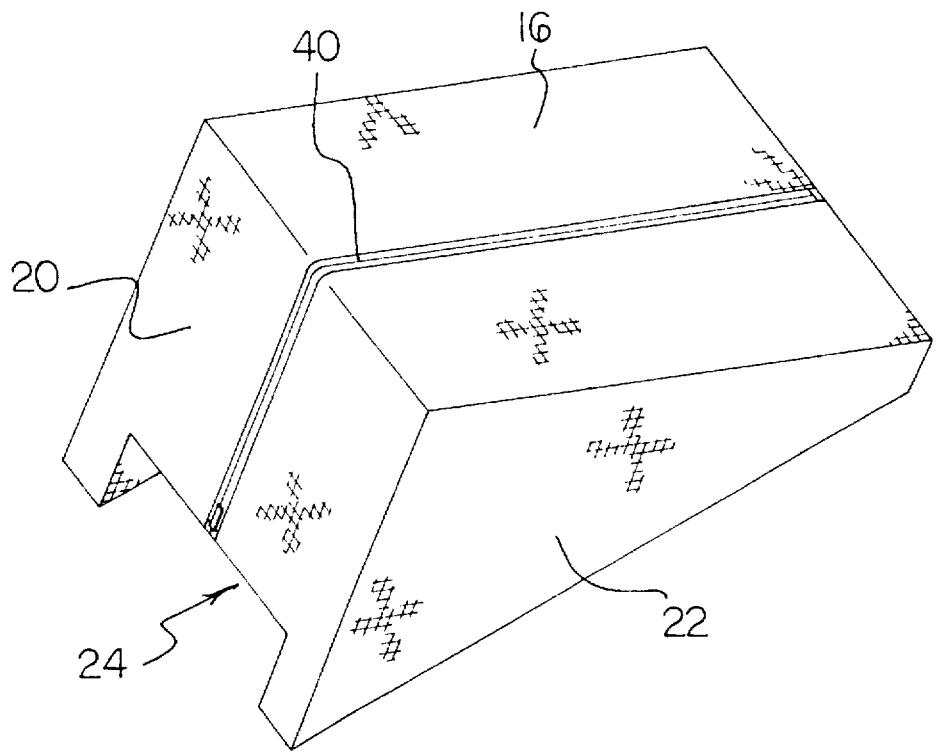
FIG. 3 is a bottom perspective view of the present invention.
Figure 4:
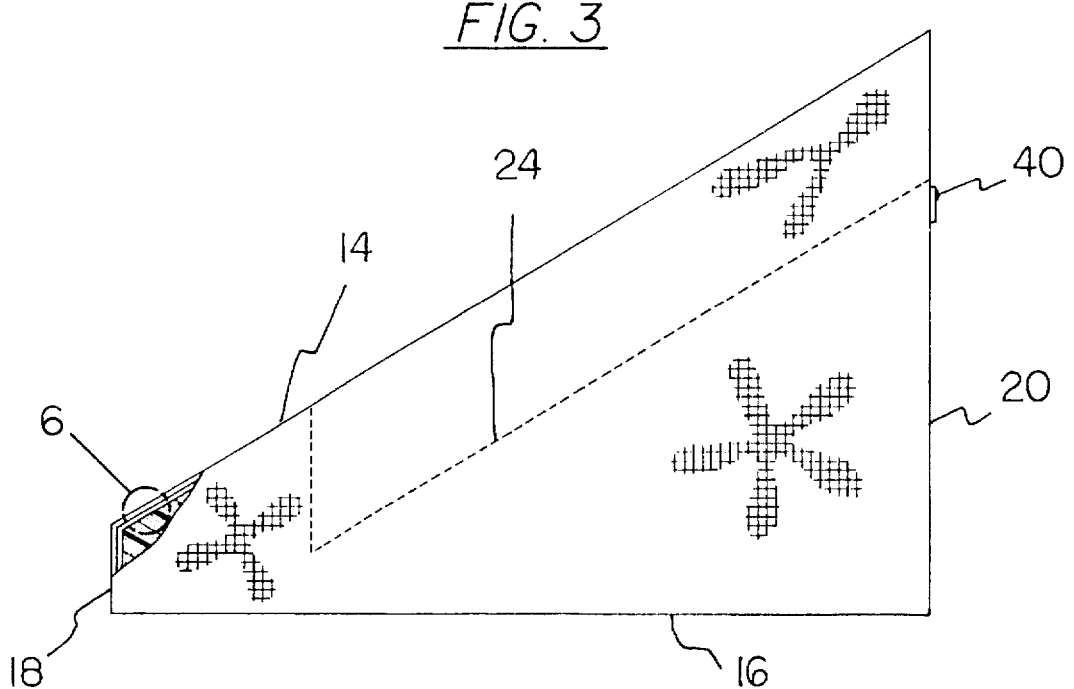
FIG. 4 is a side elevation view of the present invention.

With reference now to the drawings, and in particular, to FIGS. 1–6 thereof, the preferred embodiment of the new and improved sleeping device for infants having trachea malacia and/or gastro-intestinal reflux embodying the principles and concepts of the present invention and generally designated by the reference number 10 will be described.

Specifically, it will be noted in the various Figures that the device relates to a sleeping device for infants having trachea malacia and/or gastro-intestinal reflux for allowing an infant to sleep on their side to control trachea malacia, reflux and apnea problems. In its broadest context, the device consists of a foam wedge, a plastic casing, a fabric cover and a strap. Such components are individually configured and correlated with respect to each other so as to attain the desired objective.

The present invention is a sleep accessory designed specifically for use by infants who have trachea malacia and/or gastro-intestinal reflux.

The device 10 consists of a foam wedge 12, a plastic casing 34, a fabric cover 38 and a strap 46 with hook and loop material. The foam wedge 12 is approximately twenty inches wide, twenty-eight inches long, twenty inches tall at the high end and three inches tall at the low end. Inside the wedge 12 there is a cutout 24 in which the baby rests that also supports his/her head. A plastic casing 34 and a fabric cover 38 protect the entire wedge 12. The fabric cover 38 has a zipper up the back side so that it can be removed. The cutout area on the fabric area on the fabric cover 38 has a quilted pad 42, and a one inch fabric strap 46 over the smaller area which fastens at one end with a piece of hook and loop closure material.

The strap 46 is simply unfastened and the infant is placed in the cutout area so that the infant's head is supported. The baby may be placed on his/her side, which is the most desired position. The strap 46 is then extended across the infant to help hold him or her in place, and then fastened.

The foam wedge 12 is comprised of an upper wall 14, a lower wall 16, a front wall 18, a back wall 20, and opposed side walls 22. The upper wall 14 is angled upwardly from the front wall 18 to the back wall 20 at an angle of about forty-five degrees. The upper wall 14 has a cutout 24 formed therein. The cutout 24 extends from a position integral with the back wall 20 to a position inward the front wall 18. The cutout 24 has an upper portion 26, a lower portion 28 and an inwardly angled intermediate portion 30 therebetween. The upper portion 26 has a width about 1.5 times greater than a width of the lower portion 28. The upper portion 26 has a length greater than a length of the lower portion 28.

The plastic casing 34 is dimensioned for securement over the foam wedge 12. The plastic casing 34 is used to protect the foam wedge 12 from becoming saturated by the infant wetting.

The fabric cover 38 is dimensioned for removable coupling over the plastic casing 34 and the foam wedge 12. The fabric cover 38 includes a zippered opening 40 extending along a back and a bottom thereof to facilitate removal from the foam wedge 12. The fabric cover 38 includes a pad 42 for positioning within the cutout 24 of the foam wedge 12. The fabric cover 38 can be removed when cleaning is necessary.

The strap 46 is secured to the fabric cover 38 at a position adjacent to where the fabric cover 38 is over the cutout 24 of the foam wedge 12. A free end 48 of the strap has a hook and loop portion 50 thereon. The hook and loop portion 50 couples with a patch of hook and loop material secured on an opposing side of where the fabric cover 38 is over the cutout of the foam wedge 12.

Existing wedge sleeping supports for babies with malacia/reflux do not provide support for the infant's head. This can result in the baby's head flopping over which can lead to apnea. The existing wedges also use a fabric pocket with hook and loop straps to contain the infant on the wedge. Many infants find this so confining and uncomfortable that it interferes with their sleep. This device 10 eliminates these problems by providing the infant with head support and a cutout area in which to sleep. The support provided by the cutout 24 makes it possible to place the infant on their side, which helps to control the malacia/reflux and apnea problems.

As to the manner of usage and operation of the present invention, the same should be apparent from the above Ad description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A sleeping device for infants having trachea malacia and/or gastro-intestinal reflux for allowing an infant to sleep on their side to control trachea malacia, reflux and apnea problems comprising, in combination:

a foam wedge comprising an upper wall, a lower wall, a front wall, a back wall, and opposed side walls, the foam wedge being about 20 inches wide, 28 inches long, and between 3 and 20 inches tall, the upper wall being angled upwardly from the front wall to the back wall at an angle of about forty-five degrees, the upper wall having a cutout formed therein, the cutout extending from a position integral with the back wall to a position inward the front wall, the cutout having an upper portion, a lower portion and an inwardly angled intermediate portion therebetween, the upper portion having a width about 1.5 times greater than a width of the lower portion, the upper portion having a length greater than a length of the lower portion;

a plastic casing dimensioned for securement over the foam wedge for preventing the foam wedge from being saturated by the infant wetting;

a fabric cover dimensioned for removable coupling over the plastic casing and the foam wedge, the fabric cover including a zippered opening extending along a back and a bottom thereof to facilitate removal from the foam wedge;

a quilted pad positioned within the cut out of the foam wedge; and a strap having a width of one inch secured to the fabric cover at a position adjacent to where the fabric cover resides on the upper wall and is over the lower portion of the cutout of the foam wedge, a free end of the strap having a hook and loop portion thereon, the hook and loop portion coupling with a patch of hook and loop material secured on an opposing side of where the fabric cover resides on the upper wall and is over the cutout of the foam wedge.

* * * * *